United States Patent [19]

Klinkowstein et al.

[11] Patent Number: 4,812,775
[45] Date of Patent: Mar. 14, 1989

[54] ELECTROSTATIC ION ACCELERATOR

[75] Inventors: Robert E. Klinkowstein, Winchester; Ruth Shefer, Newton, both of Mass.

[73] Assignee: Science Research Laboratory, Inc., Somerville, Mass.

[21] Appl. No.: 72,883

[22] Filed: Jul. 20, 1987

Related U.S. Application Data

[63] Continuation-in-part of Ser. No. 857,765, Apr. 30, 1986, abandoned.

[51] Int. Cl.$^4$ .............................................. H05H 1/03
[52] U.S. Cl. .................................. 328/233; 313/359.1; 250/306; 250/299; 250/423 F; 315/111.81; 376/190
[58] Field of Search ..................... 328/233; 313/359.1, 313/360.1, 362.1, 231.01, 298; 250/306, 299, 423 F, 427; 315/111.81; 376/129, 190, 191, 196, 199, 201

[56] References Cited

U.S. PATENT DOCUMENTS

| | | | |
|---|---|---|---|
| 4,160,905 | 7/1979 | Davey | 250/306 X |
| 4,209,704 | 6/1980 | Krimmel | 376/190 X |
| 4,473,748 | 9/1984 | Konagai et al. | 250/299 |

OTHER PUBLICATIONS

Technical Description of 3.0 MV Tandetron Accelerator System 7/10/84, General Sonex Corp.
MeV Ion Beams; General Ionex Corporation, no date.
"Extraction of H$^-$ Beams from a Magnetically Filtered Multicusp Source"; York et al, Rev. Sci. Instrum. 55(5) 5/1984.
"Four Rod λ/2 RFQ for Light Ion Accelerator"; Schempp et al. Nuclear Instrum. and Methods in Physics Research, 1985.
"Water Vapor Jet target for the Charge Changing of Fast Ion Beams", Roos et al; Rev. of Sci. Instrum. 1965.
"Measurements on a dc volume H$^-$ Multicusp Ion Source for Triumf" Kendall et al, Rev. of Sci. Instrum, 1986.
"Enhancement of H$^-$ Production in a Multicusp Source by Cold Electron Injection", Leung et al, Rev. of Sci. Instrum. 1986.

Primary Examiner—David K. Moore
Assistant Examiner—K. Wieder
Attorney, Agent, or Firm—Wolf, Greenfield & Sacks

[57] ABSTRACT

A high current (0.2 to at least 2 milliamperes), low-energy (2.2 to 4 MV) ion beam is generated and is utilized to produce clinically significant quantities of medical isotopes useful in applications such as positron emission tomography. For a preferred embodiment, a tandem accelerator is utilized. Negative ions generated by a high current negative-ion source are accelerated by an electrostatic accelerator in which the necessary high voltage is produced by a solid state power supply. The accelerated ions then enter a stripping cell which removes electrons from the ions, converting them into positive ions. The positive ions are then accelerated to a target which is preferably at ground potential. For a preferred embodiment, the solid state power supply utilized to develop the required voltages is a cascade rectifier power supply which is coaxial with the accelerator between the ion source and the stripper, and is designed to have a voltage gradient which substantially matches the maximum voltage gradient of the accelerator.

27 Claims, 4 Drawing Sheets

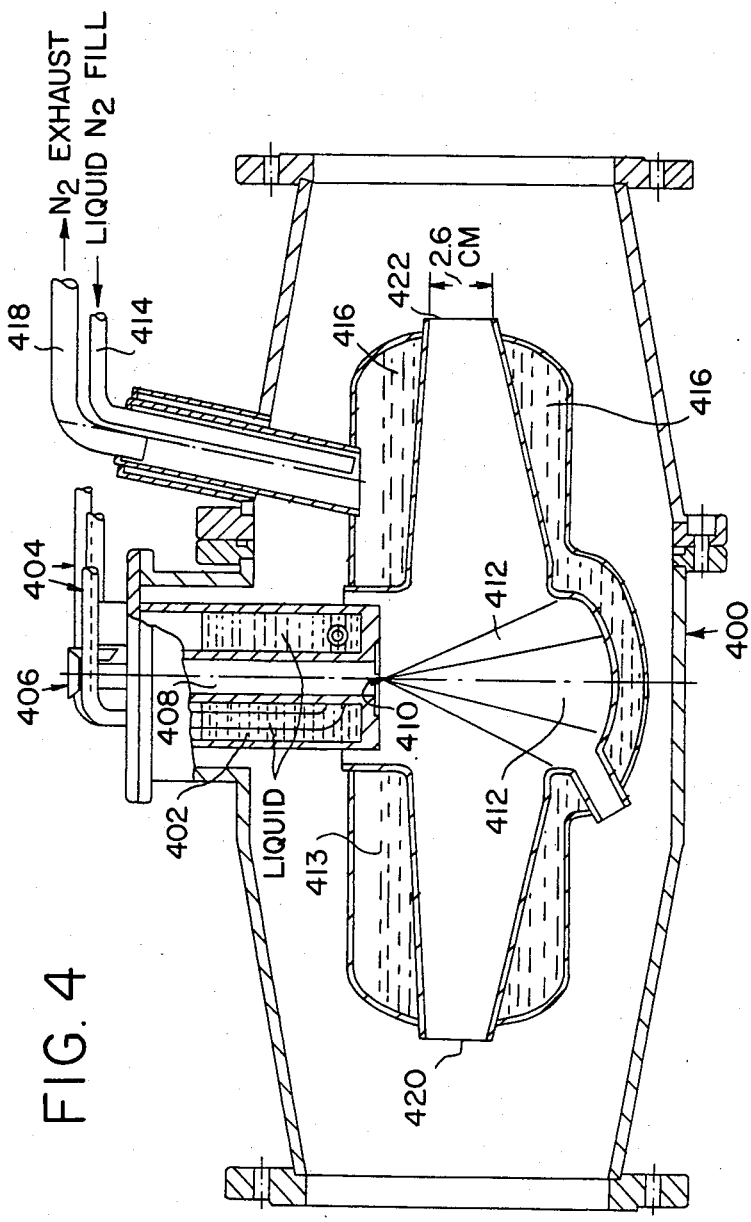

ELECTROSTATIC ION ACCELERATOR

This application is a continuation-in-part of application Ser. No. 857,765, filed Apr. 30, 1986, now abandoned.

FIELD OF THE INVENTION

This invention relates to ion accelerators and, in particular, to ion accelerators useful for generating clinically significant quantities of medical isotopes useful in applications such as positron emission tomography.

BACKGROUND OF THE INVENTION

A number of non-invasive methods of examining internal bodily organs, or sections of such organs, have become popular for diagnosing a variety of illnesses. One of these techniques is called Positron Emission Tomography (PET) or Positron Emission Transaxial Tomography (PETT). In this method of developing internal bodily images, an array of sensors detects gamma rays emitted from tissues after the subject has been administered a natural biochemical substance (for example, gases, glucose or fatty acids) into which position-emitting radio-isotopes have been incorporated. A computer calculates the paths of the gamma rays (which result from collisions of positrons and electrons) and interprets the data to generate a tomographic image. The resultant tomogram represents local concentrations of the isotope-containing substance in the tissues. By proper choice of isotope-containing substances, various processes such as brain function, local blood flow, blood volume and other metabolic processes can be studied.

The short-lived radio-isotopes are administered by intravenous injection or by having the subject inhale a gas containing small quantities of the radio-isotope. Isotopes which are often incorporated into such gases or injections are carbon-11, nitrogen-13, oxygen-15 and fluorine-18. In present PET facilities, these radio-isotopes are derived from boron, carbon, nitrogen and neon targets, respectively, by bombarding the targets with high-energy (approximately 6–15 MV) protons or deuterons obtained from a particle accelerator.

Conventionally, the acelerator which is used to produce the isotope-generating particles is a cyclotron accelerator. However, cyclotron accelerators have significant drawbacks. Due to the short half-lives of the isotopes (ranging from approximately 2 minutes for oxygen-15 to 110 minutes for fluorine-18), the accelerator must be physically located in the medical center within a short distance from the PET scanning apparatus. At present, cyclotron accelerators suitable for use in a medical environment are expensive (on the order of 1–2 million dollars); large and heavy (15 to 20 tons) and require a trained staff to operate and maintain the apparatus.

In addition, the high-energy ions produced by the cyclotron accelerator are generally used to bombard gas targets to obtain the isotopes. Gas targets must be separated from the high vacuum of the accelerator by a metallic-foil window. Because the ion beam has high energy, the window is rapidly destroyed, thus increasing the costs of maintenance and requiring highly trained operators who must disassemble the device to replace the window.

These drawbacks have restricted the use of position emission tomography to large research hospitals that have sufficient space, staff and funding to support a conventional cyclotron accelerator facility.

While smaller, lower cost, low energy ion accelerators, such as tandem Van de Graff accelerators, have existed, it has not heretofore been considered possible to use such low energy accelerators to generate clinically significant quantities of medical isotopes and such accelerators have not been capable of generating an ion beam with sufficient ion current to produce such isotopes.

Accordingly, it is an object of the present invention to provide an ion accelerator which can generate sufficient ion current in a low energy range for the production of clinically significant quantities of medical isotopes such as PET isotopes.

Another object of this invention is to provide an ion accelerator which can deliver higher currents than conventional low energy accelerators.

It is another object of the present invention to provide an ion accelerator which is smaller and lighter than existing cyclotron accelerators.

It is a further object of the present invention to provide an ion accelerator which costs less than conventional cyclotron accelerators.

It is yet another object of the present invention to provide an ion accelerator which can be easily operated by a single moderately-trained technician.

It is still a further object of the present invention to provide an ion accelerator which can operate with a solid target and thus does not require a metallic-foil window.

It is a further object of the present invention to provide an ion accelerator which has lower maintenance costs than conventional cyclotron accelerators.

SUMMARY OF THE INVENTION

The foregoing problems are solved and the foregoing objects are achieved by the method and apparatus of this invention wherein clinically significant quantities of medical isotopes are produced by bombarding a target of suitable material with a high current (0.2 to at least 2 milliampere), low-energy (2.2 to 4 MV) ion beam. In one illustrative embodiment of the invention negatively-charged ions are accelerated by means of an electrical potential generated by a solid state power supply. The accelerated ions are passed through a stripping cell which converts them into positive ions. The positive ions are then accelerated again to a target held at ground or other reference potential. With a suitably selected ion source, the accelerator is capable of producing up to a 4 MV deuteron or proton beam with a minimum delivered beam current of approximately 200 microamperes. The accelerator may be capable of delivering currents of up to approximately 2 mA, as required by the application.

As used herein, the term "solid state power supply" shall mean a power supply utilizing discrete and/or integrated electronic components such as diodes or other rectifiers, transistors, resistors, capacitors or the like, at least some of which are solid state components. A solid state power supply is to be distinguished from an electromechanical power supply such as a Van de Graff power supply. For a preferred embodiment, the solid state power supply is a cascade rectifier high-voltage supply which utilizes a plurality of voltage multiplier stages driven by a high-frequency driver circuit to accelerate negatively-charged ions (produced by a high current negative-ion source) in a high-vacuum acceleration column. The power supply is preferably coaxial with the acceleration column and is designed to have a voltage gradient which substantially matches the maximum voltage gradient of the accelerator. The accelerated ions are projected through a foil-less window into a stripping cell located within the high-voltage terminal. The stripping cell comprises a field free region in which two electrons are removed from each ion, thus converting the negative ions into positively charged ions which are then accelerated through a second, high-vacuum accelerating column to a ground-potential target. The stripping cell may comprise a vacuum chamber containing a water vapor jet or a gas stripping cell. High vacuum is maintained in the accelerator columns by means of cryo pumping of the water vapor in the high voltage terminal or by differential pumping.

Due to the simple design, the inventive electrostatic accelerator is simpler to operate, more reliable and requires far less capital outlay than that required for a conventional medical cyclotron facility. Accordingly, such an accelerator will remove a major obstacle to the widespread acceptance of PET as a diagnostic tool, thereby opening up a considerably broader market for this technology.

The inventive accelerator is capable of delivering ion beam currents of up to at least two milliamperes at energies of 2.2–4 MV. This is due to a number of factors as will be discussed hereinafter, including the high current capability of the solid state power supply. These factors, therefore, significantly increase the operating range of the accelerator as compared with another common tandem configuration, such as the tandem Van de Graff. A Van de Graff power supply is typically restricted to currents of under 200 microamperes which is insufficient for PET applications.

In the higher current (I=1–2 mA) configuration, the inventive accelerator may also be used in another medical application, that of producing epithermal neutrons for the destruction of tumor cells. In this application, called "neutron capture therapy", epithermal neutrons would be produced by bombarding a lithium target with a 2.5 MV, 1 mA proton beam from the inventive accelerator. Compact, lightweight accelerators capable of delivering proton beams with these parameters are currently not available.

BRIEF DESCRIPTION OF THE DRAWINGS

FIG. 4 is a cross-sectional view of a water vapor jet stripper suitable for use in practicing the teachings of this invention.

DETAILED DESCRIPTION OF THE PREFERRED EMBODIMENT

At the present time there are a number of short-lived radioisotopes which have clinical significance for use with PET technology. These radioisotopes are commonly produced by bombarding a target with accelerated deuterons. The relevant properties of several of these radioisotopes are summarized below in Table I.

TABLE I

| Isotope | Reaction | Threshold Energy (MeV) | Energy at X-section Max. (MeV) | Half Life (min) |
|---|---|---|---|---|
| Carbon-11 | $^{10}B(d,n)^{11}C$ | 0 | 2.3 | 20.4 |
| Nitrogen-13 | $^{12}C(d,n)^{13}N$ | 0.3 | 2.3 | 9.98 |
| Oxygen-15 | $^{14}N(d,n)^{15}O$ | 0 | 2.5 | 2.04 |
| Fluorine-18 | $^{20}Ne(d,\alpha)^{18}F$ | 0 | — | 110 |

The reactions illustrated are relatively simple; for example in the production of Oxygen-15, Nitrogen-14 is bombarded with deuterons and releases a neutron becoming oxygen-15. Typically, carbon-11 would be obtained by bombarding a target formed of a boron containing substance such as one containing boron-10, nitrogen-11 would be obtained from a target of a carbon containing substance such as one containing carbon-12, oxygen-15 would be obtained from a target of a nitrogen containing substance such as one containing nitrogen-14 and fluorine-18 would be obtained for a target of a neon containing substance such as one containing neon-20.

The deuteron reactions listed in Table I are characterized by their low threshold energies (typically under 1 MV) and by cross-sections which peak at low incident energies (typically below 3 MV). The threshold energy is the lowest energy at which the reaction will take place and the maximum cross section energy is the incident deuteron energy which has the highest probability of reacting with the target nucleus. Table I indicates that low energy deuterons may be used to produce the relevant isotopes. In the discussion below, the production of Oxygen-15 is chosen as an example because of its clinical importance in PET technology. However, the conclusions and techniques disclosed below are also applicable to the production of carbon-11, nitrogen-13 and fluorine-18.

Figure 1:
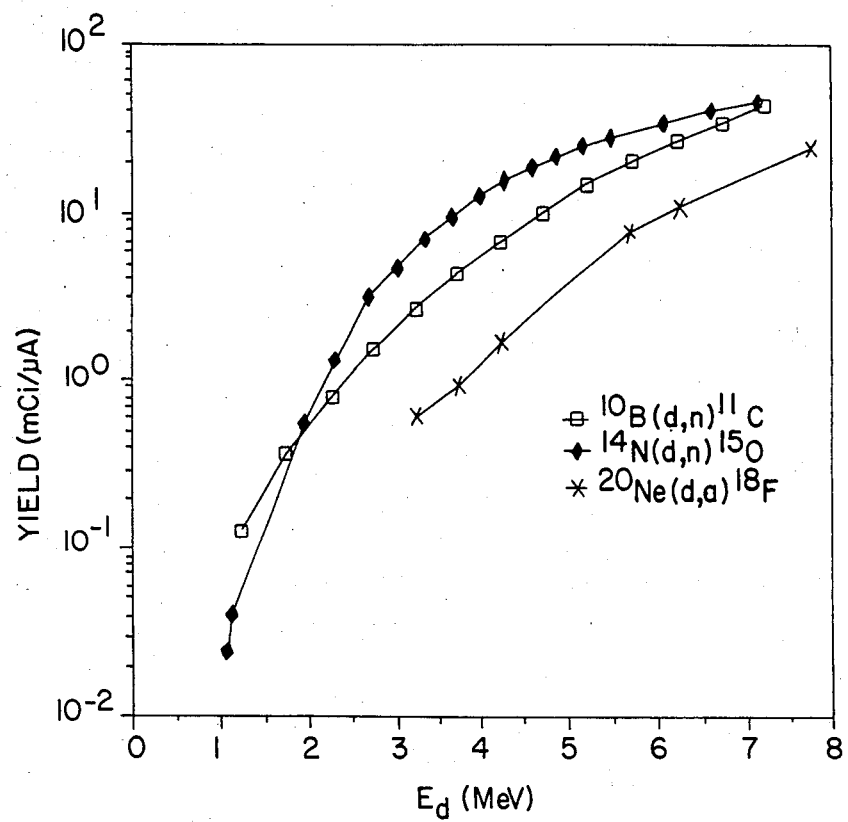
FIG. 1 is a plot of the calculated saturated yields of oxygen-15, carbon-11 and fluorine-18 as a function of the bombarding deuteron energy.

The inventive ion accelerator may be used with solid targets, thus eliminating the requirement of a metallic foil window to separate the accelerator vacuum from the target gas. In order to produce a sufficient amount of the oxygen-15 isotope for use with existing PET technology, a yield of at least 0.2 Ci of oxygen-15 must be obtained. The oxygen-15 yield at saturation in a lithium-nitride target is plotted as a function as incident deuteron energy in FIG. 1. The curve in FIG. 1 is a theoretical curve which can be calculated from published cross sections for the nitrogen-14/oxygen-15 reaction and from known stopping powers for ions in materials. FIG. 1 shows that from 1–10 mCi/$\mu$A of oxygen-15 can be obtained with an incident energy of 2.2–4.0 MV, respectively. Thus, for a 200 microampere beam, clinically significant oxygen-15 activity can be produced at a deuteron energy of 2.2 MV. At the high end of the energy range, oxygen-15 yields exceeding those which may be obtained with medical cyclotrons may be produced by the inventive accelerator. At 4 MV, the fluorine-18 yield is about a factor of ten lower than the oxygen-15 yield. Therefore, currents in the range of 1–2 mA will be required for fluorine-18 production.

Figure 2:
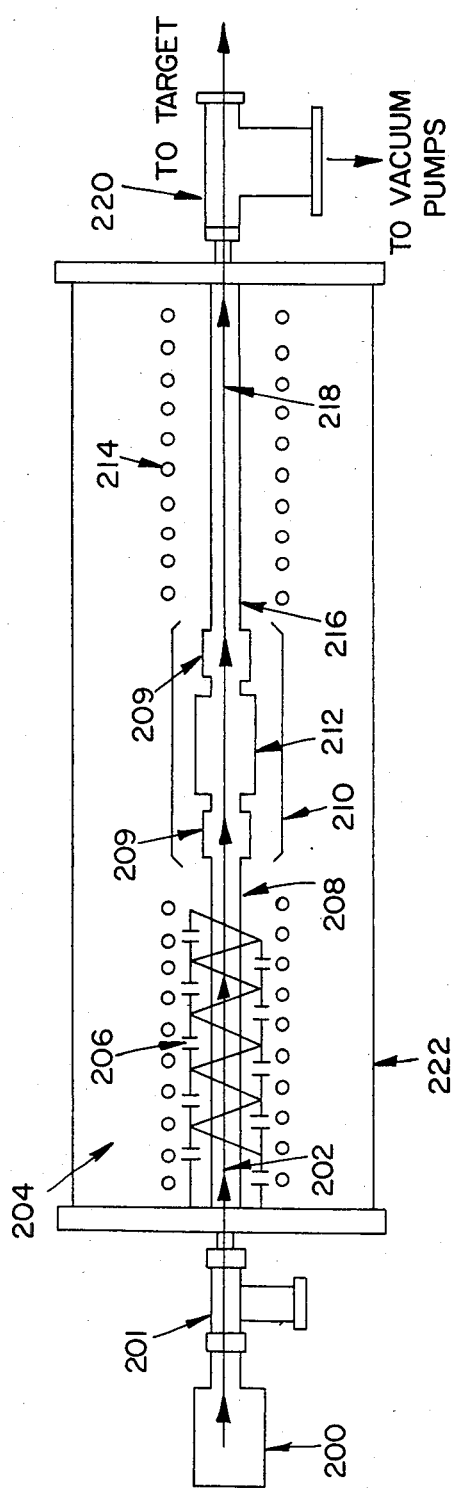
FIG. 2 is a schematic view of the overall construction of the inventive tandem ion accelerator utilizing a cascade rectifier power supply.

The beam parameters required by the reactions illustrated in FIG. 1 to obtain significant quantities of oxygen-15, carbon-11 and fluorine 18 may be obtained by using the electrostatic accelerator shown in schematic form in FIG. 2 to accelerate deuterons to the required energy.

In the accelerator, a negative-ion beam 202 (D−) generated by source 200 is continuously injected at low energy into the accelerating column 208. Negative ion source 200 may be a magnetically filtered volume production negative-ion source. The construction and operation of such a negative ion source is discussed in "Extraction of H- Beams from a Magnetically-Filtered Multi cusp Source", R. L. York, R. R. Stevens, Jr., K. N. Leung and K. W. Ehlers, *Review of Scientific Instruments*, Volume 55, pg. 681 (1984); "The Development of a High current H Injector for the Proton Storage Ring at LAMPF", R. L. York, R. R. Stevens, Jr., R. A. DeHaven, J. R. McConnell, E. P. Chamberlin and R. Kandarian, *Nuclear Instruments and Methods in Physics Research*, B 10/11, pg. 891 (1985); "Measurements on a dc volume H multicusp ion source for TRIUMF", K. R. Kendall, M. McDonald, D. R. Mosscrop, P. W. Schmor, and D. Yuan, *Review of Scientific Instruments*, Volume 57, pg. 1277 (1986); "Enhancement of Hproduction in a multicusp source by cold electron injection", K. N. Leung, K. W. Ehlers, and R. V. Pyle, *Review of Scientific Instruments*, Volume 57, pg. 321 (1986). The discussed volume production negative-ion sources are compact and capable of supplying ion currents of up to approximately 20 milliamperes.

The negative-ion beam 202 is injected at low energy into accelerating column 208 which is maintained at high vacuum by means of vacuum pumps attached to tee fitting 201. The beam is attracted to and accelerated by voltage supplied to high-voltage terminal 210. The voltage is created and maintained by means of cascade rectifier circuit 206 connected between source 200 and voltage terminal 210. In accelerator column 208, the ion beam attains an energy of $qV_t$ where $V_t$ is the potential of the high-voltage terminal with respect to ground and q is the charge of the negative ion.

A stripping cell 212 is located in terminal 210 and converts the negative-ion beam into a positive-ion beam with high efficiency. The stripping cell, which consists of a foil-less, field-free cell, may, for example, be a conventional gas stripping cell, but is preferably a water jet stripping cell. The construction and operation of the gas stripping cell is well known while the construction and operation of a water jet stripping cell is described in "Water Vapor Jet Target for the Charge Changing of Fast Ion Beams", M. Roos, P. H. Rose, A. B. Wittkower, N. B. Brooks, and R. P. Bastide, *Review of Scientific Instruments*, Volume 36, Number 4 (Apr. 1965).

If a gas stripping cell is utilized, a number of different gas types can be used for the stripping gas. Illustratively, nitrogen ($N_2$) may be used because of its relatively high stripping cross-section and equilibrium fraction for the formation of positively-charged deutron ions.

However, while the efficiency for conversion of negative deuteron ions to positive deuteron ions may, in principle, be close to 100% for a beam energy of greater than 300 KV, in practice, conversion efficiencies of only approximately 70% are normally achieved in gas stripping cells due to limitations in cell thickness and scatter losses. This means that a higher current ion source must be utilized for the source 200 in order to achieve a desired ion current at the target.

By contrast, the water vapor jet stripper can provide conversion efficiencies of greater than 90%. The superior pumping speed of the water jet stripper coupled with the liquid nitrogen-cooled surfaces of the stripper which freeze stray water and prevent drifting into the accelerating chambers which would contaminate these chambers, permit this stripper to operate with lower vacuum pressure and to have very large (i.e. 2.6 cm diameter) entrance and exit apertures. This reduces the alignment problems associated with the smaller diameter apertures which must be used in gas jet strippers to avoid causing contamination, and permits larger ion current to flow.

FIG. 4 shows a cross section of a water vapor jet stripper 400 suitable for use in the ion accelerator shown in FIG. 2. In this stripper, water in reservoir or boiler 402 is heated by freon gas flowing through heating tubes 404 immersed in the water. The heated water forms water vapor, the pressure of which is a function of the water temperature. The water vapor passes through a needle valve which is controlled by control 406, reaching sonic velocity as it passes through the valve, and then expands in expansion chamber 408. The temperature and pressure of the vapor are reduced on passing through the needle valve, but the vapor is reheated in the expansion chamber, the walls of which are at the temperature of boiler 402. The vapor temperature returns very nearly to the original temperature, but at greatly reduced pressure. At the end of the expansion chamber, the heated water vapor passes through a sonic nozzle 410. The resulting water vapor jet 412 produced by the sonic nozzle is confined to an approximately 60° expansion angle because of its high speed flow (in the order of Mach 1). The water vapor is collected by a condenser 413, the walls of which are maintained at a temperature of approximately −164° C. by liquid nitrogen in contact with the condenser walls, the liquid nitrogen being provided through tube 414 to reservoir 416 and the heated nitrogen gas being exhausted through tube 418. Since the water vapor jet is directed at condenser 413 at high speed and freezes when coming in contact with the condenser, thereby sticking thereto, water vapor does not flow from the stripper 400 into either of the accelerating chambers, permitting relative large entrance and exit apertures, 420 and 422 respectively, to be utilized. As previously indicated, this enhances the ion current carrying capacity of the ion accelerator. This also reduces the load on the vacuum pumps required to avoid contamination of the accelerating columns.

From high-voltage terminal 210, the positive-ion beam 218 is accelerated through accelerator column 216 and tee fitting 220 to the target (not shown) which is preferably maintained at ground potential. High vacuum is maintained between stripping cell 212 and accelerator columns 208 and 216 by cryo-pumping in the terminal stripper (by for example differential pumping elements 209) or by other standard, suitable means.

In order to prevent sparkover, the entire apparatus is sealed in a pressure chamber 222 which is filled with a high pressure insulating gas 204 for example, sulphur hexafluoride ($SF_6$). In addition, conventional high voltage grading rings 214 are provided in order to evenly spread the high-voltage potential across the accelerating column.

Figure 3:
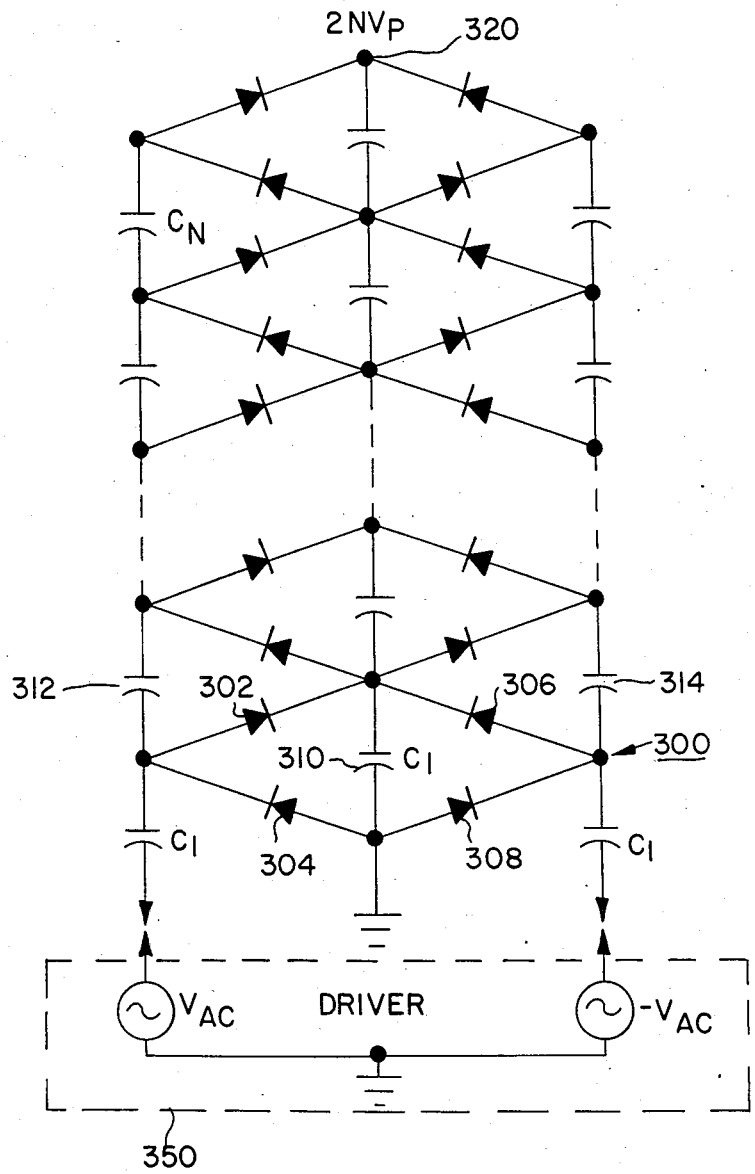
FIG. 3 is a schematic diagram of a cascade rectifier circuit used to generate the accelerating potential.

FIG. 3 is a schematic diagram of the cascade rectifier circuit which may be used to generate the accelerating potential. The cascade rectifier circuit consists of a number of identical stages 300 each of which consists of four diodes, 302–308 and a capacitor 310. The stages are coupled by additional capacitors 312 and 314. In accordance with well-known circuit theory, the high-voltage terminal 320, of this circuit attains a voltage of $2NV_p$ under no load conditions where N is the number of multiplier stages and $V_p$ is the peak center voltage of the high-frequency driver circuit 350. However, when subjected to a load current (I) the output voltage, $2NV_p$, drops by an amount given by:

$$V_D = \frac{I}{12fC}(2N^3 + 3N^2 + N) \quad (1)$$

(where f is the frequency of the driver and C is the capacitance pe stage) and exhibits a voltage ripple of:

$$V_R = \frac{IN}{2fC} \quad (2)$$

From equation (1), it is evident that the driver frequency (f) and the capacitance per stage (C) should be as large as possible to obtain good voltage stability for a given load current (I). The size and capacity of a power supply suitable for integration into accelerating column 208 (FIG. 2) depends on the physical dimensions and voltage ratings of the capacitors 310-314 which are used in each of the power supply stages.

For example, in the illustrative accelerator it may be desired to generate a 3.8 MV deuteron beam with a current of 1 mA. This beam will produce an oxygen-15 activity level of approximately 10 Ci of oxygen-15 or 1 Ci of fluorine-18. Since the illustrative accelerator produces an output beam energy of twice the accelerating potential, a 1.9 MV high-voltage potential must be produced by the cascade rectifier circuit. In the illustrative design, a capacitance of 0.006 uf per stage is chosen with a driver frequency of 40 KiloHertz. With these parameters, each stage produces a 50 kV potential and, thus, 40 stages are needed to generate the 1.9 MV terminal potential when voltage droop is taken into account.

The tandem configuration requires that the power supply deliver twice the final beam current and thus for a delivered beam current of 1 milliampere, the current, I, in equations (1) and (2) is 2 milliamperes. The capacitance and frequency parameters discussed above yield a loaded output voltage droop and ripple given by equations (1) and (2) of 92 kilovolts and 208 volts, respectively. Thus, the illustrative 40-stage cascade rectifier circuit produces an actual terminal voltage of 1.91 MV and a beam energy of 3.82 MV for a delivered beam current of 1 milliampere.

The length of the cascade rectifier 206 and thus of accelerator column 208 is dictated by the physical size of the capacitors. Capacitors with values suitable for use with the preceding illustrative power supply are commercially available from High Energy Corporation, located at Lower Valley Road, Parkersburg, Pa., and are cylindrically packaged with a diameter of 2.5 inches and a length of 1.0 inch. The resulting 3.8 MV accelerator would require a negative-ion accelerating column of approximately 1.0 meter in length to accommodate the capacitors. The power supply electric field gradient will be 19.7 kv/cm which will match the maximum voltage gradient of the accelerating column. This permits optimum acceleration of the ion beam in chamber 206 while minimizing the overall size of the system through use of the coaxial configuration. A similar length would be used for the positive ion accelerator column. Thus, the accelerator would have an overall length of approximately 2.5 meters (including the stripping cell) and a diameter (dictated by high-voltage standoff requirements) of approximately 1 meter.

Illustratively, the inventive accelerator can be used with solid targets to avoid the use of a metallic foil window at the beam output. Such windows require frequent maintenance due to damage by the deuteron beam. Alternatively, a solid target bombarded by accelerated deuterons can be used to generate oxygen-15 or other isotopes. The oxygen-15 can be released from the solid target by means of a number of conventional techniques including dissolving the target in a suitable solvent.

While for the preferred embodiment of the invention, a tandem accelerator has been illustrated as the means of producing the high current, low energy ion beam for producing medical isotopes, and such a tandem accelerator is clearly superior in terms of size, cost, complexity, and ease of use and maintenance to any other ion accelerator currently known for producing such isotopes with a high current, low energy ion beam, it is within the contemplation of the invention to produce such isotopes using any suitable low energy, high current ion source. An example of an ion source capable of providing the required currents at low energy levels, although at much higher cost, and with a much larger and more complex piece of equipment, is a radio-frequency quadrupole (RFQ) accelerator of the type described in "Four-Rod- /2-RFQ for Light Ion Acceleration", A. Schempp, H. Deitinghoff, M. Ferch, P. Junior and H. Klein, *Accelerator Technology*, Volume VIII, pg. 831 (1985). As previously indicated, conventional wisdom has heretofore been that it would not be possible to generate clinically significant quantities of medical isotopes in such an environment.

While th invention has been described above with respect to a preferred embodiment thereof, the foregoing and other changes in form and detail may be made therein without departing from the spirit and scope of the invention.

What is claimed is:

1. An electrostatic ion accelerator comprising:
    a negative ion source adapted for generating a minimum ion current of approximately 0.2 milliamperes,
    a high voltage terminal,
    a stripping cell located in said terminal,
    a first accelerating column connected between said ion source and said stripping cell,
    a second accelerating column connected between said stripping cell and said target,
    means connected to said first and second accelerating columns for maintaining a high vacuum therein, and
    solid state power supply means connected to said ion source and said terminal for supplying a positive potential of at least 1MV to said terminal.

2. An accelerator according to claim 1 wherein said solid state power supply means is coaxial with said first accelerating column and has a voltage gradient which substantially matches the maximum voltage gradient of said accelerating column.

3. An accelerator according to claim 2 wherein said solid state power supply means is a cascade rectifier power supply.

4. An accelerator according to claim 1 wherein said solid state power supply means is a cascade rectifier power supply.

5. An accelerator according to claim 1 wherein said solid state power supply supplies a positive potential of approximately 1.1 to 2MV.

6. An accelerator according to claim 1 wherein said stripping cell is a field-free gas-filled cell.

7. An accelerator according to claim 1 wherein said stripping cell is a water vapor jet stripper.

8. Apparatus for producing medically active radioisotopes by bombarding targets maintained at substantially ground potential with accelerated ions, said apparatus comprising
- a negative ion source adapted for generating a minimum ion current of approximately 0.2 milliamperes,
- a high-voltage terminal,
- a stripping cell located in said terminal,
- a first accelerating column connected between said ion source and said stripping cell,
- a second accelerating column connected between said stripping cell and said target,
- means connected to said first and said second accelerator columns for maintaining a high-vacuum therein, and
- means connected to said ion source and said terminal for supplying a positive potential of less than 2 MV to said terminal.

9. Apparatus as claimed in claim 8 wherein said radioisotope is oxygen-15, and
wherein said target is a nitrogen-containing substance.

10. Apparatus as claimed in claim 8 wherein said radioisotope is carbon-11, and
wherein said target is a boron-containing substance.

11. Apparatus as claimed in claim 8 wherein said radioisotope is nitrogen-13, and
wherein said target is a carbon-containing substance.

12. Apparatus as claimed in claim 8 wherein said radioisotope is fluorine-18, and
wherein said target is a neon-containing substance.

13. Apparatus as claimed in claim 8 wherein said means for supplying a positive potential includes a cascade rectifier power supply electrically connected to said ion source and said terminal, said power supply comprising a plurality of voltage multiplier stages.

14. Apparatus as claimed in claim 13 wherein said cascade rectifier power supply is coaxial with said first accelerating column, and
wherein the voltage gradient of said power supply is substantially equal to the maximum voltage gradient of the first accelerating column.

15. Apparatus as claimed in claim 8 wherein said stripping cell is a field-free gas-filled cell.

16. Apparatus as claimed in claim 8 wherein said stripping cell is a water vapor jet stripper.

17. Apparatus as claimed in claim 8 wherein said means for supplying a positive potential supplies a potential of approximately 1.1 to 2MV.

18. Apparatus as claimed in claim 8 wherein said target is a solid target.

19. A method for producing medically active radioisotopes by bombarding a target of a suitable substance and maintained at a reference potential with accelerated ions, said method comprising the steps of:
generating an ion beam from an ion beam source, said ion beam having a minimum ion current of approximately 0.2 milliamperes; and
accelerating the ion beam from the ion source to the target, the final beam energy at the target being in the range of approximately 2.2 to 4 MV.

20. A method as claimed in claim 19 wherein said accelerating step includes the steps of accelerating said ion beam through a first accelerating column, the voltage drop across the first accelerating column being in the range of approximately 1.1 to 2 MV, reversing the polarity of said ion beam, and accelerating the ion beam with its polarity reversed through a second accelerating column to the target, the voltage drop across the second column being substantially the same as the voltage drop across the first column.

21. A method as claimed in claim 20 wherein said ion beam source is a negative ion beam source;
wherein said polarity reversing step includes the step of stripping electrons from the accelerated negative ions in a stripping cell to generate a positive ion beam output; and
wherein the positive ion beam is accelerated to the target.

22. A method as claimed in claim 19 wherein said radioisotope is oxygen-15; and
wherein said target is a nitrogen containing substance.

23. A method as claimed in claim 19 wherein said radioisotope is carbon-11; and
wherein said target is a boron containing substance.

24. A method as claimed in claim 19 wherein said radioisotope is nitrogen-13; and
wherein said target is a carbon containing substance.

25. A method as claimed in claim 19 wherein said radioisotope is fluorine 18; and
wherein said target is a neon containing substance.

26. A method for producing medically active radioisotopes by bombarding a target maintained at substantially ground potential with accelerated ions, said method comprising the steps of:
generating a negative ion beam having a minimum ion current of approximately 0.2 milliamperes;
accelerating said ion beam through a first accelerating column, the voltage drop across the first accelerating column being less than 2MV;
stripping electrons from the accelerated negative ions in a stripping cell to generate a positive ion beam output; and
accelerating the positive ion beam through a second accelerating column to the target, the voltage drop across the second column being substantially the same as the voltage drop across the first column and the beam current at the target being a minimum of approximately 0.2 milliamperes.

27. Apparatus for producing epithermal neutrons for medical treatment of tumors comprising
an ion source for generating an ion current of at least one milliampere,
a high voltage terminal,
a stripping cell located within the high-voltage terminal,
a lithium target,
a first accelerating column connected between said ion source and said stripping cell,
a second accelerating column connected between said stripping cell and said target,
means connected to said first and second accelerator columns for maintaining a high vacuum therein, and
a solid state power supply electrically connected to said ion source and said high-voltage terminal for supplying a positive high-voltage potential of at least 1 MV to said terminal.

* * * * *